(12) United States Patent
Hendriksen et al.

(10) Patent No.: US 8,561,967 B2
(45) Date of Patent: *Oct. 22, 2013

(54) DEVICE FOR LOADING A SELF EXPANDABLE PROSTHESIS INTO A SHEATH

(75) Inventors: Per Hendriksen, Herlufmagle (DK); Allan G. Hemmingsen, Jystrup M. (DK); Jacob Lund Clausen, Kgs. Lyngby (DK)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/528,265

(22) Filed: Jun. 20, 2012

(65) Prior Publication Data

US 2012/0259403 A1 Oct. 11, 2012

Related U.S. Application Data

(62) Division of application No. 12/283,718, filed on Sep. 15, 2008, now Pat. No. 8,220,121.

(60) Provisional application No. 60/993,837, filed on Sep. 14, 2007.

(51) Int. Cl.
*H02G 1/08* (2006.01)

(52) U.S. Cl.
USPC ............ 254/134.3 FT; 254/134.3 R

(58) Field of Classification Search
USPC ............ 29/235, 271, 255, 263, 280; 254/134.3 FT See application file for complete search history.

(56) References Cited

U.S. PATENT DOCUMENTS

| | | | |
|---|---|---|---|
| 2,946,560 A | 7/1960 | Ferm | |
| 3,037,744 A | 6/1962 | Cooper | |
| 3,052,450 A | 9/1962 | Trunnell | |
| 5,897,102 A | 4/1999 | Sorkin | |
| 6,047,954 A * | 4/2000 | Griffioen | 254/134.4 |
| 8,220,121 B2 * | 7/2012 | Hendriksen et al. | 29/235 |
| 2005/0218386 A1 * | 10/2005 | Giroux | 254/134.3 FT |
| 2009/0076585 A1 * | 3/2009 | Hendriksen et al. | 623/1.12 |
| 2012/0259403 A1 * | 10/2012 | Hendriksen et al. | 623/1.12 |

\* cited by examiner

*Primary Examiner* — Lee D Wilson
(74) *Attorney, Agent, or Firm* — Brinks Hofer Gilson & Lione

(57) ABSTRACT

An assembly comprising: a protective sheath and a loading device for loading a self-expandable prosthesis into the sheath, the loading device having a conical distal section, which radially compresses the prosthesis and an annular lip that engages with the interior of the distal end of the sheath to guide the prosthesis into the sheath while protecting the sheath from damage.

16 Claims, 2 Drawing Sheets

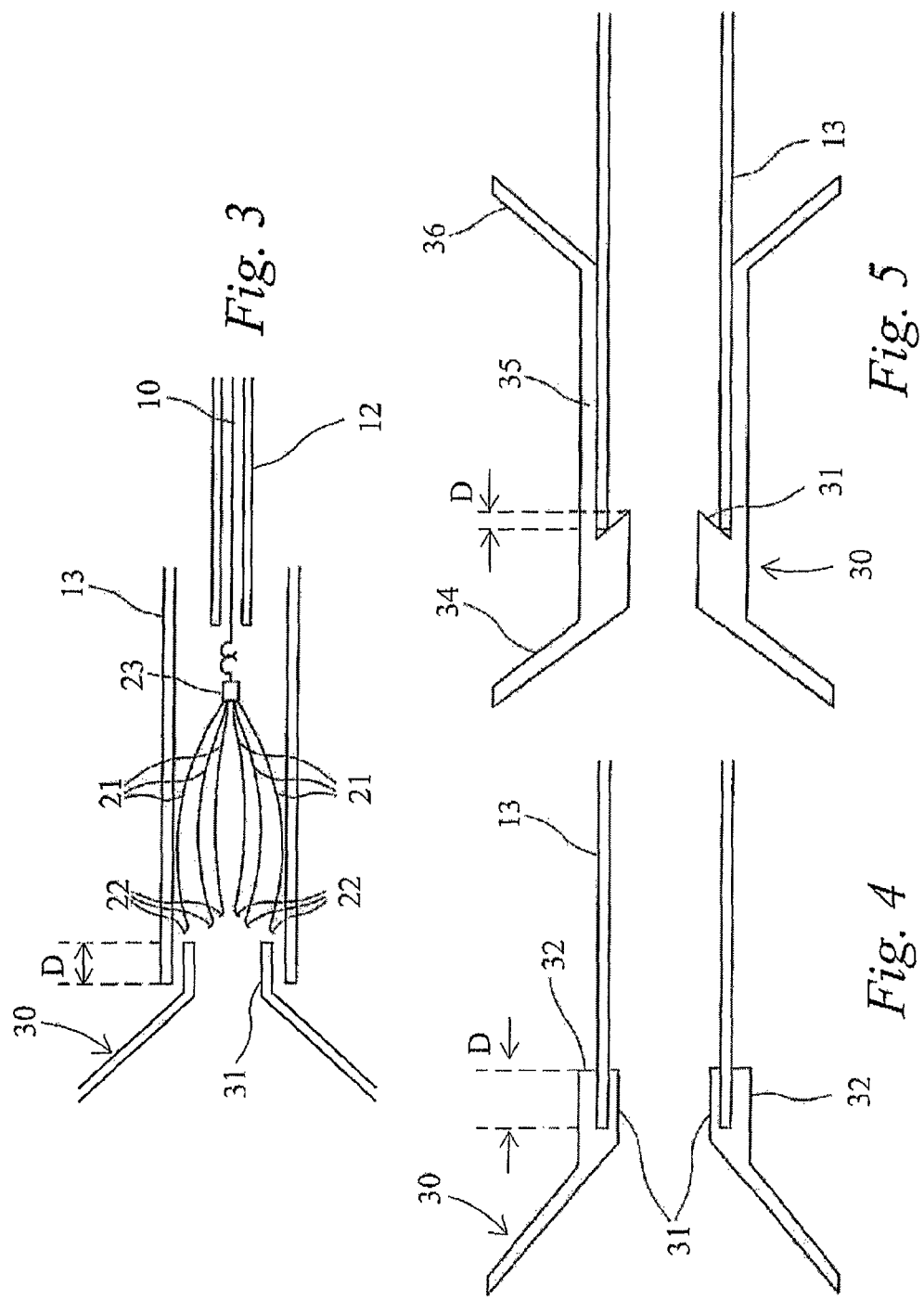

DEVICE FOR LOADING A SELF EXPANDABLE PROSTHESIS INTO A SHEATH

CROSS-REFERENCE TO RELATED APPLICATIONS

This patent application is a divisional of co-pending U.S. patent application Ser. No. 12/283,718, filed Sep. 15, 2008, which application claims priority of provisional application Ser. No. 60/993,837, filed Sep. 14, 2007 entitled "Device for Loading A Self-Expandable Prosthesis Into A Sheath," the entire contents of which are incorporated herein by reference.

TECHNICAL FIELD

The present invention relates to medical devices and may find particular application in a device for loading a self-expandable prosthesis into a protective sheath.

BACKGROUND OF THE INVENTION

A wide variety of self-expandable prostheses is known in the art such as stents or embolic filters. Many such self-expandable prostheses are made from elastic materials such as stainless steel and Conichrome™—a cobalt-chromium-nickel-molybdenum-iron alloy. Such devices are typically introduced percutaneously to the patient; for example, filtering devices that are percutaneously placed in the vena cava have been available for over thirty years. Such percutaneous methods typically rely on these elastic prostheses being radially compressed so as to adopt a low profile configuration within an introducer sheath. In more detail, the prosthesis is typically attached to a stylet housed within a cannula, the cannula passing through the lumen of the sheath. The prosthesis may be fixed to the stylet by way of an attachment hook or snare at the distal end of the stylet cooperating with a feature on the proximal end of the prosthesis. The stylet is withdrawn within the cannula so that the prosthesis is mounted adjacent the distal end of the cannula, whereupon the stylet is locked relative to the cannula so that axial movement is prohibited thereafter and the prosthesis is held securely in position. The cannula-stylet assembly is then retracted, pulling the attached prosthesis into the lumen of the introducer sheath. During this part of the procedure it is necessary to radially compress the prosthesis so that it will fit within the lumen of the introducer sheath. This is commonly performed by a loading device at the distal end of the introducer sheath.

It has been found that maintaining an elastic prosthesis in a stressed configuration, for example the low profile configuration within the sheath, leads to degradation of the prosthesis owing to mechanical stresses within the prosthesis structure. Therefore, it is preferable for the prosthesis to be delivered to the surgeon or medical technician in an unstressed configuration. Typically this is done by performing the locking and mounting steps outlined above, but leaving the attached prosthesis outside the distal end of the introducer sheath. A handle is provided at the proximal end of the cannula to allow the surgeon or medical technician to retract the cannula and pull the prosthesis within the sheath. The entire apparatus, including the loading device, is provided assembled and hermetically sealed to the surgeon or medical technician, so that loading of the prosthesis may be accomplished simply by retracting the handle.

It has been found during such loading operations that often the distal end of the prosthesis will protrude from the distal end of the introducer sheath after the loading operation has been performed. Further, where the prosthesis comprises barbs for engagement with body lumens, these are likely to catch the open end of the introducer sheath, requiring a surgeon or technician's direct intervention; thus, it may be impossible to complete the loading without loss of sterility. Further, the barbs may scratch the interior of the introducer sheath and produce debris. The resulting debris may potentially be fatal if it is carried away during the procedure by the blood stream and lodges in a sensitive part of the vasculature—for example the lungs, where it may cause a pulmonary embolism.

Thus, there exists a need for a loading device which ensures correct placement of the prosthesis within an introducer sheath and also substantially prevents damage to the introducer sheath during loading of the prosthesis.

SUMMARY OF THE INVENTION

Thus there is provided in accordance with a first aspect of the present invention a device for loading a self-expandable prosthesis into a protective sheath comprising:
a passageway through said apparatus extending along an axis and having a proximal and a distal end, said passageway comprising:
  a distal section and a proximal section adjacent said distal section;
  wherein the radius of said distal section decreases with distance from the distal end to a first value adjacent a rim of said loading device, said rim extending axially into said proximal section.

According to a second aspect of the present invention there is provided an assembly comprising:
  a protective sheath having interior and exterior radii and a distal end;
  and a loading device for loading a self-expandable prosthesis into said sheath, the loading device comprising:
  a passageway through said device extending along an axis and having a proximal and a distal end, said passageway comprising:
  a distal section where the radius decreases with distance from the distal end to a first value at a rim of said loading device, the first value being less than the interior radius of said sheath; the passageway further comprising a proximal section harbouring said sheath;
  said rim extending axially so as to engage with the interior of the distal end of said sheath and prevent distal movement of said sheath relative to said device.

According to a third aspect there is provided an assembly comprising:
  a self-expandable prosthesis releasably attached to the distal end of a wire;
  a protective sheath having interior and exterior radii and a distal end; and
  a loading device for loading a self-expandable prosthesis into said sheath, the loading device comprising:
    a passageway through said device extending along an axis and having a proximal and a distal end;
    a conical section surrounding a distal portion of said passageway, the conical section narrowing with distance from the distal end of said passageway
    a rim extending located proximally to said conical section, the rim extending axially so as to engage with the interior of the distal end of said sheath and prevent distal movement of said sheath relative to said device;
  wherein, said wire extends axially through said passageway and along the lumen of said protective sheath and wherein said rim prevents said prosthesis from contacting the distal end of said sheath during loading.

According to a fourth aspect there is provided a method for loading a self-expandable prosthesis into a protective sheath, the method comprising the steps of:
providing a loading device having a passageway extending along an axis and having a proximal and a distal end, wherein the radius of said passageway decreases with distance from the distal end to a first value adjacent a rim of said loading device;
engaging said rim with the interior of the distal end of said protective sheath;
urging said prosthesis proximally from a distal end of said passageway through said passageway so as to radially compress said prosthesis and into sheath, said rim serves to prevent contact between the prosthesis and the distal end of the sheath.

Further objects, features and advantages of this invention will become readily apparent to persons skilled in the art after a review of the following description, with reference to the drawings and claims that are appended to and form a part of this specification.

BRIEF DESCRIPTION OF THE DRAWING

The present invention will now be described with reference to the figures in which:

FIG. 3 displays the same apparatus as FIG. 1, with the loading operation having been completed and the prosthesis being harboured within the lumen of the sheath.

FIG. 4 displays a loading device in accordance with a further embodiment of the present invention engaged with a sheath.

FIG. 5 displays a loading device in accordance with a still further embodiment of the present invention, also engaged with an introducer sheath.

DETAILED DESCRIPTION

Figure 1:
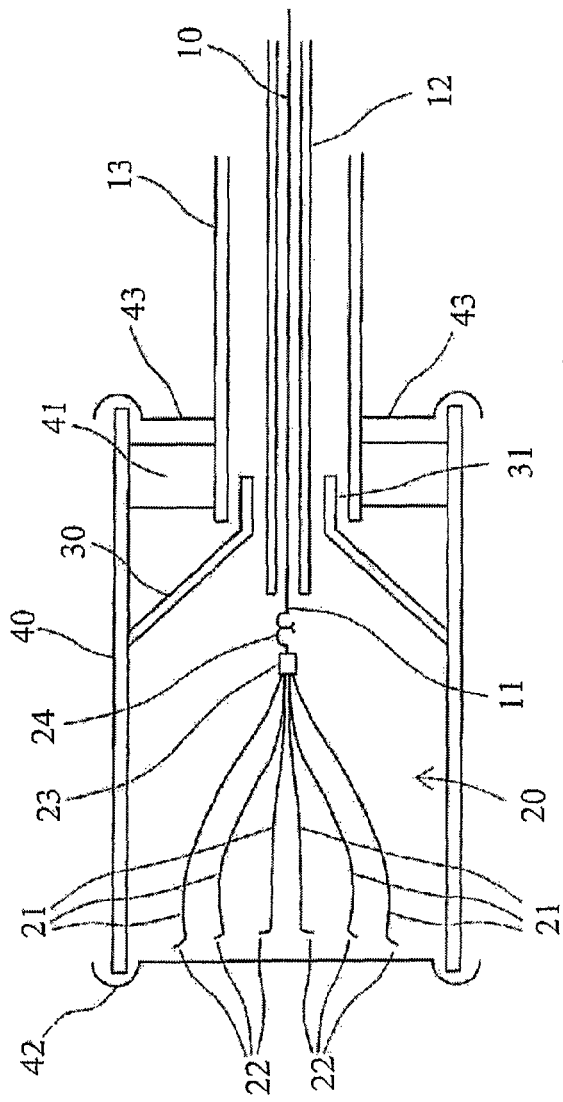
FIG. 1 shows the distal end of an apparatus including a loading device in accordance with a first embodiment of the present invention and a prosthesis in a relaxed configuration awaiting loading into the sheath.

FIG. 1 displays an apparatus including a loading device (30) according to an embodiment of the present invention. The apparatus also includes an introducer sheath (13), of which the distal end is pictured, having a cannula-stylet assembly (10, 12) running through its lumen and protruding from the distal end of the introducer sheath (13). The distal end of the stylet has an attachment hook (11) which is engaged with an attachment hook (24) on the proximal end of an embolic filter (20). The filter (20) has a plurality of struts (21) attached at their respective proximal ends to a single filter hub (23) on which is located the attachment hook (24); each strut (21) has a radially outfacing barb (22) for engagement with a luminal wall. The loading device (30) pictured in FIG. 1 is substantially conical in shape and has an annular lip (31) which protrudes within the interior of the distal end of the introducer sheath (13). The annular lip (31) provides a rim, which in use protects the distal end of the introducer sheath. The apparatus further includes first housing member (40) shaped substantially as a tube and a second substantially annular housing member (41). The first housing member (40) radially encloses the prosthesis (20), the loading device (30) and the distal end of the introducer sheath; the annular form of the second housing member (41) substantially encircles the distal end of the introducer sheath and contacts at its radially exterior surface the first housing member (40) so as to prevent tilting of the first housing member (40) and thus the loading device (30). The apparatus also includes a first substantially circular sealing member (42) and a second substantially annular sealing member (43). The first sealing member (42) is located at the distal end of the first housing member (40) and has an annular rim to hermetically seal the distal end of the first housing member (40); the second sealing member (43) is has a radially interior edge which is sealingly attached to the introducer sheath (13) and a radially exterior annular lip which is sealingly attached to the proximal end of the first housing member (40).

Figure 2:
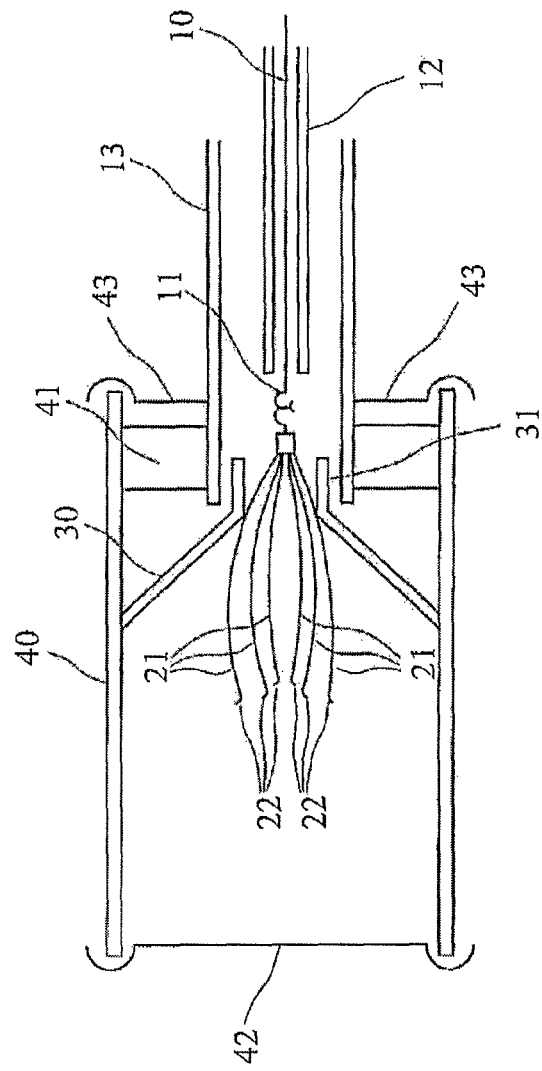
FIG. 2 displays the apparatus of FIG. 1, with the prosthesis undergoing radial compression during the loading procedure.

FIG. 2 shows the same apparatus with the cannula-stylet assembly (10, 12) being retracted proximally through the lumen of the introducer sheath (13), thus pulling with it the prosthesis (20). The loading device (30) contacts the struts (21) of the filter (20) and owing to its conical shape gradually compresses the filter (20). As displayed in FIG. 2, the barbed distal ends of the struts (22) are forced inwards by the action of the loading device (30).

FIG. 3 shows the apparatus with the filter (20) fully retracted into the distal end of the lumen of the introducer sheath (13). The barbs at the distal ends of the struts of the filter (22) have been guided by the loading device (30) to a distance D from the distal end of the introducer sheath (13). Thus, the filter (20) is loaded in a position spaced from the end of the introducer sheath (13), so avoiding firstly catching the barbs (22) on the distal end of the introducer sheath (13) and secondly dragging the barbs of the filter (22) along the interior of the sheath which might risk damage to the interior surface. Further, there is clearly no risk of the struts (21) protruding from the distal end of the introducer sheath (13) once the loading device (30) has been removed. The annular lip (31) thus provides a rim, which in use protects the distal end of the introducer sheath by engaging with the interior of the distal end of the sheath. Those skilled in the art will appreciate that the distance D may be varied to suit the particular filter or prosthesis being mounted.

FIG. 4 shows a loading device (30) according to a further embodiment of the present invention, having a similar conical shape to the device of FIG. 1, but having two annular lips (31, 32) at its proximal end to engage with the distal end of the introducer sheath (13). The interior (31) and exterior (32) lips extend parallel to the longitudinal axis of the sheath (13) in the proximal direction and receive the distal end of the introducer sheath in the annular groove created between the two lips. The depth of this groove thus dictates the spacing D of the prosthesis (not shown) from the end of the introducer sheath. The interior (31) and exterior (32) lips thus provide a rim, which in use protects the distal end of the introducer sheath by engaging with the interior of the distal end of the sheath. The rim also acts to prevent distal movement of the sheath (13) relative to the loading device (34). This construction also substantially prevents tilting of the loading device (30) relative to the longitudinal axis of the sheath.

FIG. 5 displays a loading device (30) in accordance with a still further embodiment of the present invention having two conical (34, 36) ends linked by a tubular passageway (35). The proximal conical end (36) guides and receives the distal end of the introducer sheath (13) into the tubular passageway (35), the passageway being matched to the shape and size of the sheath to ensure a snug fit. Towards the distal end of the passageway there is provided an annular lip (31) that extends proximally so as to define an annular groove around its radial exterior. The annular lip (31) may be partially frustoconical in shape, so that a normal to its radially exterior surface defines a substantially constant angle with the proximal direction along the axis of the tubular passageway; this angle is preferably acute. In use, the distal end of the introducer sheath (13) is harboured within this annular groove, so that the annular lip (31) extends proximally a distance D into the lumen of the distal end of the sheath. Therefore, a prosthesis (not shown) being loaded through the distal end of the loading device (30) will not contact the interior wall of the introducer sheath until it has travelled at least distance D into the lumen of the sheath. The annular lip (31) thus provides a rim, which in use protects the distal end of the introducer sheath by engaging with the interior of the distal end of the sheath. The rim also acts to prevent distal movement of the sheath (13) relative to the loading device (34). The conical section at the distal end of the loading device (34) acts to radially compress the prosthesis as in the embodiments of FIGS. 1-4.

Whilst the above descriptions relate to the loading of an embolic filter into the lumen of a sheath the teachings may equally be applied to the loading of other self-expandable prostheses. In particular, the specifications of the loading device may be altered so as to provide a suitable spacing D from the end of the introducer. In the case of an embolic filter it is the distal end that must be guided precisely into the sheath, however with other prostheses it may be necessary to guide the proximal end or indeed any point along the length of the prostheses into place. This may be accomplished by an apparatus which provides a much larger spacing D so that the desired point along the length of the prosthesis comes into contact with the interior of the introducer and then the loading device may be withdrawn distally so as to allow the remainder of the prosthesis to be unsheathed by the loading device. It should be noted that the cannula may have to be fixed in position whilst this occurs so that the prosthesis does not move distally during removal of the loading device.

Further, while the forgoing description has referred to a process in which the prosthesis is pulled via an attachment to a stylet at its proximal end those skilled in the art will appreciate that various loading techniques may be performed in accordance with the teachings of the invention. For example, the stylet may be attached at any point along the length of the prosthesis or the prosthesis may urged by pushing from its distal end. Indeed, many methods in which the prosthesis is gradually moved from in a proximal direction through the loading device might be adopted.

Further, it should be appreciated that the loading device need not be strictly confirmed to the shapes disclosed here above, it being sufficient that the device provides a passageway that tapers from its distal end and has a rim that extends axially into the lumen of the sheath to guide the prosthesis to its desired location.

It is envisaged that loading devices according to the present invention may be manufactured from materials such as glass or metals, for example stainless steel. Indeed, any material that is both harder than the material of the prosthesis so as to be resilient to scratching of its interior surface and sufficiently rigid in order to be able to compress radially the prosthesis to the desired configuration may be appropriate.

As a person skilled in the art will readily appreciate, the above description is meant as an illustration of implementation of the principles this invention. This description is not intended to limit the scope or application of this invention in that the invention is susceptible to modification, variation and change, without departing from spirit of this invention, as defined in the following claims. In particular, where specific combinations of features are presented in this specification, which includes the following claims and the drawings, those skilled in the art will appreciate that the features may be incorporated within the invention independently of other disclosed and/or illustrated features.

What is claimed is:

1. Apparatus for loading a self-expandable prosthesis into a protective sheath comprising:
   a passageway through said device extending along an axis and having a proximal and a distal end, said passageway comprising:
   a distal section and a proximal section adjacent said distal section;
   wherein the radius of said distal section decreases with distance from the distal end to a first value adjacent a rim of said loading apparatus, said rim extending axially into said proximal section.

2. Apparatus according to claim 1, wherein said proximal section of said passageway has a radius of a second value greater than the exterior radius of said rim.

3. Apparatus according to claim 1, wherein said rim is annular in shape.

4. Apparatus according to claim 1, wherein the portion of said loading apparatus surrounding the distal section of said passageway is substantially conical.

5. An assembly comprising:
   a protective sheath having interior and exterior radii and a distal end; and
   a loading device for loading a self-expandable prosthesis into said sheath, the loading device comprising:
   a passageway through said device extending along an axis and having a proximal and a distal end, said passageway comprising:
   a distal section where the radius decreases with distance from the distal end to a first value at a rim of said loading device, the first value being less than the interior radius of said sheath; the passageway further comprising a proximal section harbouring said sheath;
   said rim extending axially so as to engage with the interior of the distal end of said sheath and prevent distal movement of said sheath relative to said device.

6. Apparatus according to claim 5, wherein said rim prevents said prosthesis from contacting the distal end of said sheath during loading.

7. Apparatus according to claim 5, wherein said proximal section of said passageway has a radius at least equal to the exterior radius of said sheath.

8. Apparatus according to claim 5, wherein said rim is formed as an annular lip having an exterior radius at most equal to the interior radius of said sheath.

9. Apparatus according to claim 5, further comprising a self-expandable prosthesis.

10. Apparatus according to claim 9 contained within hermetically sealed container.

11. An assembly comprising:
    a self-expandable prosthesis releasably attached to the distal end of a wire;
    a protective sheath having interior and exterior radii and a distal end; and
    a loading device for loading a self-expandable prosthesis into said sheath, the loading device comprising:
    a passageway through said device extending along an axis and having a proximal and a distal end;
    a conical section surrounding a distal portion of said passageway, the conical section narrowing with distance from the distal end of said passageway
    a rim extending located proximally to said conical section, the rim extending axially so as to engage with the interior of the distal end of said sheath and prevent distal movement of said sheath relative to said device;

wherein, said wire extends axially through said passageway and along the lumen of said protective sheath and wherein said rim prevents said prosthesis from contacting the distal end of said sheath during loading.

12. Apparatus according to claim 11, wherein said loading device further comprises a tubular section extending along said axis from said conical section, said tubular section radially surrounding said rim.

13. Apparatus according to claim 12, wherein said rim is formed as an annular lip.

14. Apparatus according to claim 13, wherein said rim has an exterior radius at most equal to the interior radius of said sheath.

15. Apparatus according to claim 14, wherein the exterior radius of said rim decreases with distance from the distal end of the passageway so that the radially exterior surface is substantially frustoconical.

16. Apparatus according to claim 11 contained within a hermetically sealed container.

\* \* \* \* \*